United States Patent [19]

Davies

[11] Patent Number: 4,482,538

[45] Date of Patent: Nov. 13, 1984

[54] NAIL VARNISH COMPOSITION CONTAINING NITROCELLULOSE, ABRASIVE PARTICLES AND COLLOIDAL SILICA

[76] Inventor: Aulette Davies, 45 Arend Ave., Randpark Ext. 5, Randburg, Transvaal, South Africa

[21] Appl. No.: 369,151

[22] Filed: Apr. 16, 1982

[30] Foreign Application Priority Data

Apr. 16, 1981 [ZA] South Africa ............... 81/2562

[51] Int. Cl.³ ............... A61K 7/04; C08K 3/36; C08L 1/14
[52] U.S. Cl. ............... 424/61; 106/193 J; 106/195
[58] Field of Search ............... 424/61; 106/193 J, 195

[56] References Cited

U.S. PATENT DOCUMENTS

| | | | |
|---|---|---|---|
| 3,609,102 | 10/1969 | Schlossman | 424/168 |
| 4,040,857 | 2/1975 | Lissant | 424/168 |
| 4,144,081 | 3/1979 | van der Heem | 106/193 J |
| 4,158,571 | 6/1979 | Lynch et al. | 106/272 |
| 4,197,212 | 4/1980 | Minton et al. | 252/164 |
| 4,263,051 | 4/1981 | Crawford et al. | 106/195 X |

FOREIGN PATENT DOCUMENTS

1177420 1/1970 United Kingdom.

OTHER PUBLICATIONS

Chem. Abs., 98: 185401w.

Primary Examiner—Sidney Marantz
Assistant Examiner—Shawn P. Foley
Attorney, Agent, or Firm—Young & Thompson

[57] ABSTRACT

A coating composition for applying to human nails which has a liquid base, generally including a resin, solvent and colloidal silica, having suspended therein fine abrasive particles such as diamond particles. The liquid base must be a Bingham plastic having a yield stress of not less than 0.2 Pa.

6 Claims, 2 Drawing Figures

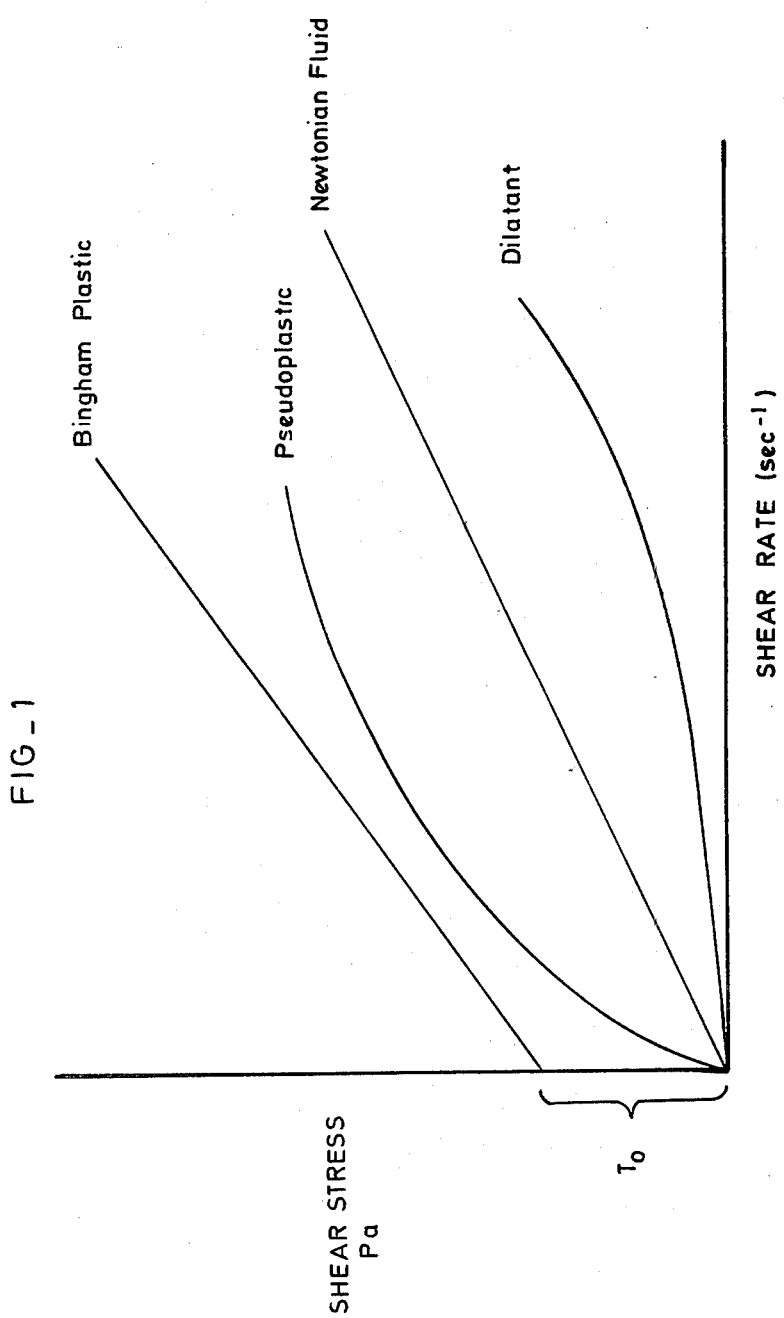

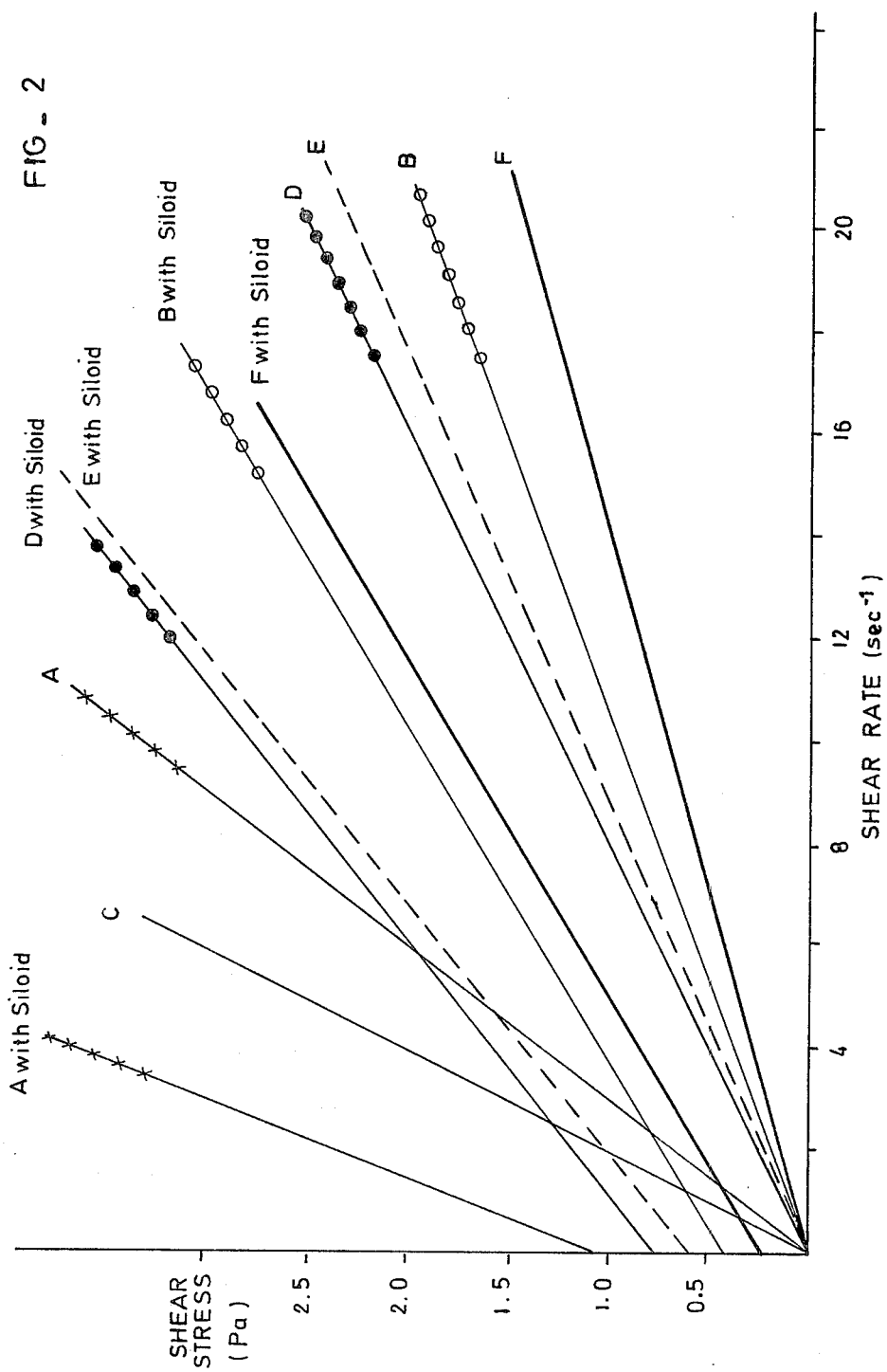

NAIL VARNISH COMPOSITION CONTAINING NITROCELLULOSE, ABRASIVE PARTICLES AND COLLOIDAL SILICA

BACKGROUND OF THE INVENTION

This invention relates to a coating composition and more particularly to a coating composition for applying to human finger- or toe-nails.

It has been proposed to incorporate diamond particles in nail varnishes and polishes. Such varnishes or polishes have the effect of providing the nails with particularly wear-resistant coating. In the case of varnishes, the diamond particles may also have the effect of providing the coating with a sparkle. Nail varnishes and polishes have a liquid base comprising a resin and a solvent and also generally include a plasticizer and pigments. One of the main problems which presents itself when incorporating diamond particles in nail varnishes and polishes is the difficulty of maintaining the diamond particles in suspension. The diamond particles must be maintained in suspension for a reasonable period for otherwise the product will be commercially unacceptable.

SUMMARY OF THE INVENTION

According to the present invention, there is provided a coating composition for applying to human nails including a liquid base adapted to be applied to a nail to provide a coating thereon and having suspended therein fine abrasive particles, the liquid base being a Bingham plastic having a yield stress of not less than 0.2 Pa.

DESCRIPTION OF THE DRAWING

FIGS. 1 and 2 illustrate graphically shear stress v shear rate plots for various types of fluids.

DETAILED DESCRIPTION OF THE INVENTION

Newton defined viscosity as the ratio of the shear stress (force per unit area) required to maintain a given shear rate in the flow of a fluid. For gases and liquids and for solutions that are 'chemically simple' or of low molecular weight, it is found that viscosity is constant with respect to shear rate. Such fluids are known as Newtonian fluids and a plot of shear stress against shear rate will give a straight line through the origin.

For some other fluid-like materials, either the viscosity is not constant and/or the flow behaviour cannot be fully described by viscosity alone. These are known as non-Newtonian fluids and examples are polymer melts, solutions of high molecular weight, biological fluids, colloidal suspensions and clay suspensions. There are, however, a number of non-Newtonian fluids whose flow behaviour can be accurately described by a knowledge of their viscosity. They are known as purely-viscous non-Newtonian fluids and can be classified as either pseudoplastic or dilatant depending on whether the viscosity decreases or increases with the shear rate.

There are certain non-Newtonian fluids which will not flow unless the shear stress exceeds a critical value. Such fluids, which are said to possess a yield stress and whose viscosities remain constant with respect to shear rate, are known as Bingham plastics.

FIG. 1 illustrates graphically typical plots obtained of shear stress (in Pa) v shear rate (in sec$^{-1}$) for a Bingham plastic, a pseudoplastic, a Newtonian fluid and a dilatant. $T_o$ is the yield stress for the Bingham plastic.

Essential to the present invention is that the liquid base is a Bingham plastic having a yield stress of not less than 0.2 Pa, generally not less than 0.5 Pa. It has been found that if the liquid base is not a Bingham plastic having this minimum yield stress the fine abrasive particles will settle out of the composition. The yield stress value of the Bingham plastic in some cases attained a value of 1.0 Pa or higher. For larger particles Bingham plastics of higher yield stresses will generally be used and for smaller particles Bingham plastics of lower yield stresses will generally be used. In all cases the yield stress will not be less than 0.2 Pa.

The liquid bases for most commercially available nail varnishes or polishes comprise a resin and solvent and usually also contain a plasticizer and pigment. The resins can be nitrocellulose or dinitrocellulose. Nitrocellulose films tend to shrink, so that their surface adhesion may be only moderate. Other resins such as formaldehyde resins, may, therefore, be added to impart adhesion. Gloss and plasticizers are added to reduce shrinkage and make the film flexible.

The solvents used influence the ease of application of the varnish, its rate of drying and hardening and final characteristics of the film. The preferred solvents for such compositions are mixtures of low and medium boiling point alcohols, aromatic hydrocarbons and aliphatic hydrocarbons.

Plasticizers may be added singly or in combinations of two or more, depending on the formulation. High molecular weight esters may be used as well as castor oil. The esters are typically dibutyl and dioctyl phthalate, triethyl citrate, and acetyl tributyl citrate.

The pigments used may be carbon black, iron oxides, chromium oxides, ultramarines and metallic powders. Transparent systems require the use of solvent-soluble colourants such as D and C red, green, yellow and violet.

The liquid bases of all the commercially available nail varnishes examined by the applicant exhibit pure Newtonian characteristics, i.e. all points in the shear stress/shear rate plot lie on a straight line which upon extrapolation passes directly through the origin. It has been found that such bases can be converted into bases having Bingham plastic characteristics by adding thereto colloidal silica i.e. of millimicron size such as that sold under the trade mark Aerosil or Siloid. The colloidal silica is simply mixed with the varnish thereby creating a liquid base having the desired characteristics. The amount of colloidal silica added will depend on the nature of the starting liquid base and the yield stress which is desired to be obtained.

The abrasive particles which are suspended in the liquid base are fine and generally have a particle size of less than 30 microns. Typically, the particle size will be in the range 6 to 12 microns. Examples of suitable abrasive particles are diamond, cubic boron nitride, alumina, glass beads and mixtures thereof. The preferred abrasive particle is diamond.

The amount of abrasive particle suspended in the liquid base will depend on the nature of the application and the effect desired. Generally, the abrasive particle content will not exceed 2.5 gms (about 12 to 13 carats) per 100 ml of liquid base.

A number of commercially available nail varnishes were obtained and viscosity measurements made. The viscosity of each varnish was measured without any additions thereto and then another viscosity measurement was taken after 1.6 carats of Siloid per 15 ml of liquid base had been added thereto. The yield stress for each liquid base to which the Siloid was added was also determined.

The viscosity measurements were made using a commercially available instrument of the coaxial cylinder type, i.e. a Ferranti portable viscometer. The operation of the instrument is as follows:

The head of the viscometer is immersed in a beaker of the fluid to be measured. The fluid is sheared in the small gap between the inner and outer cylinders, the latter cylinder being driven by a synchronous motor through a gear box. The viscous torque on the inner cylinder is balanced against a spiral spring and indicated by a pointer against a graduated scale. Three interchangeable gear boxes of either three or five speeds are used to give a range of speeds from 1 to 300 rpm. The spring fitted to the instrument gives maximum torque of 20 gm/cm. A range of cylinder sizes are also available. To minimize end effects, the inner cylinders are specially shaped and guard-rings are used. The combination of gear boxes and cylinders allows a shear stress of up to 700 Pa and shear rates between 0.8 to 950 sec$^{-1}$ to be obtained. The range of viscosity covered is from 0.2 to 20,000 poise.

The minimum sample size used was 100 ml and all measurements were conducted at 20° C.

The results obtained in these experiments are tabulated below in Table 1.

TABLE 1

| Nail Varnish Type | Viscosity BEFORE (cP) | Viscosity WITH Siloid (cP) | Yield Stress (Pa) |
|---|---|---|---|
| A | 330 | 650 | 1.11 |
| B | 95 | 180 | 0.4 |
| C | 500 | | |
| D | 125 | 200 | 0.79 |
| E | 114 | 205 | 0.59 |
| F | 70 | 152 | 0.27 |

Plots of shear stress v shear rate for each of the above varnishes, with and without Siloid, can be found set out in FIG. 2.

It was found that the nail varnishes A, B, D, E, and F after the Siloid had been added thereto produced liquid bases which were capable of maintaining up to 2.5 gms of fine diamond particles per 100 ml of liquid base without any detactable settling of the diamond particles for periods of 30 days and longer. The very viscous varnish C to which no Siloid was added exhibited pure Newtonian characteristics (i.e. no yield stress) and was found not to be capable of achieving this.

In all the tests carried out above, the diamond particles had a particle size in the range 6 to 12 microns and these particles were simply mixed with the liquid base to produce the suspension.

A number of compositions for applying to fingernails were prepared. In all cases, a standard varnish liquid base A as identified in Table 1 was used. This base included a nitrocellulose resin and a solvent. To the liquid base was added, by mixing, 1.6 carats of Siloid per 15 ml of liquid base. Suspended in the base was a variety of abrasive particles as set out below in Table 2.

TABLE 2

| Example | Diamond | Alumina | Glass beads |
|---|---|---|---|
| 1 | 0.5 | 0.4 | — |
| 2 | 0.5 | 0.2 | 0.2 |
| 3 | 0.4 | 0.25 | 0.25 |
| 4 | 0.5 | — | 0.4 |
| 5 | 0.1 | — | 0.8 |

The quantities given above are carats per 15 ml of liquid base. The diamond powder used had a particle size in the range 6 to 12 microns while the alumina used had a particle size of less than 24 microns. In each case the particles were maintained in suspension for a long period of time.

I claim:

1. In a nail varnish for applying to human nails, the varnish comprising a liquid base which is a solution of a nitrocellulose in a solvent; the improvement in which the varnish contains an effective amount up to about 2.5 g/100 ml of abrasive particles having a particle size of less than about 30 microns, said abrasive particles being selected from the group consisting of diamond, cubic boron nitride, alumina, glass beads and mixtures thereof, said amount being effective to improve the wear resistance of the varnish, the varnish also containing colloidal silica in an amount effective to impart to said varnish properties of a Bingham plastic having a yield stress of not less than 0.2 Pa.

2. Nail varnish as claimed in claim 1, in which said yield stress is not less than 0.5 Pa.

3. Nail varnish as claimed in claim 1, in which said yield stress is not less than 1.0 Pa.

4. Nail varnish as claimed in claim 1, in which said abrasive particles have a particle size in the range of 6 to 12 microns.

5. Nail varnish as claimed in claim 1, in which the abrasive particles are diamond.

6. Nail varnish as claimed in claim 1, in which the amount of colloidal silica is about 1.6 carats/15 ml of varnish.

* * * * *